United States Patent [19]

Sulepov

[11] Patent Number: 4,669,464
[45] Date of Patent: Jun. 2, 1987

[54] SURGICAL INSTRUMENT FOR TRANSJUGULAR VENOUS THROMBOECTOMY

[76] Inventor: Eugenio P. Sulepov, Braille, 30-7o C, Fuencarral (Madrid), Spain

[21] Appl. No.: 708,232

[22] Filed: Mar. 5, 1985

[30] Foreign Application Priority Data

Mar. 6, 1984 [ES] Spain .................................... 530325

[51] Int. Cl.⁴ .......................................... A61B 17/00
[52] U.S. Cl. ............................................... 128/303 R
[58] Field of Search ............. 128/328, 320, 356, 346, 128/326, 348.1, 327, 303 R

[56] References Cited

U.S. PATENT DOCUMENTS

| 668,647 | 2/1901 | Jaenicke | 128/320 |
| 1,677,671 | 7/1928 | Councill | 128/328 |
| 4,557,255 | 12/1985 | Goodman | 128/345 X |

Primary Examiner—Michael H. Thaler
Attorney, Agent, or Firm—Ladas & Parry

[57] ABSTRACT

A surgical instrument for use in transjugular venous thromboectomy, comprising a shorter tube and a longer tube in a parallel, back-to-back relationship, each of the tubes having two ends, a first end of said longer tube having a widening provided with a first handle, a second end of the longer terminating in a stopper provided with two axial holes, a first end of the shorter tube having an oblique bending close to a point at which the longer tube widens, a second end of said shorter tube terminating at a distance before the second end of the longer tube; a rod within the longer tube, a first end of which, protruding from the widening, terminates in a second handle, and a second end of which is connected to a clamp which presses two ends of a steel cable passing through the axial holes of the stopper, thereby forming a loop whose eye may be increased or reduced until it is closed, axial displacement of the rod being guided, without rotation, by grooves in the widening of said longer tube; a wire fixed at a first end thereof to the second end of the shorter tube, a second end of the wire being rotatingly secured to a midpoint of the loop; a tubular network, one side of which is attached to the longer tube, one end of a second side of which is fixed to the second end of the shorter tube and a second end of said second side of which is fixed to the steel cable forming the loop, the wire being placed inside of the network; and a screw for fixing position of the rod after movement thereof relative to said first tube.

3 Claims, 3 Drawing Figures

SURGICAL INSTRUMENT FOR TRANSJUGULAR VENOUS THROMBOECTOMY

The present invention refers to a surgical instrument for transjugular venous thromboectomy, whereby recently formed occlusive and/or floating thrombi are excised, after the extension limits thereof have been determined by phlebography.

Pulmonary thromboembolism is the blocking of the network of the pulmonary artery by previosly broken away thrombi. Its etiology is considered in accordance with the nature and source of the embolus. Almost all pulmonary emboli orginate as thrombi in the veins or in the cavities of the right part of the heart. The sources of pulmonary thromboembolism were located, by autopsies, mainly in the MSIS veins, in the pelvic veins and in the right part of the heart, the superior vena cava.

Massive pulmonary thromboembolisms, that is, those which affect the main pulmonary artery or its primary branches, are the main cause of sudden death. Application of retrograde iliocavography in cases of severe iliofemoral venous thrombosis revealde in 55% of such cases the existence of asymptomatic floating thrombi in the inferior vena cava, iliac and femoral veins which are, by themselves, a potential source of massive pulmonary embolism. The progress made in vascular surgery facilitated patients suffering fron venous obstruction to be surgically operated and preventive surgery to be practised in pulmonary thromboembolism.

Procedures for the surgical prophylaxis of pulmonary artery thromboembolisms are direct and indirect. The direct procedures are carried out upon exposure of the inferior cava and/or iliac veins by means of laparotomy or retroperitoneal access. The indirect procedures are carried out without laparotomy and separation of the inferior cava, introducing an artificial obstacle within the cavity thereof through a peripheral vein.

One characteristic of the direct procedure resides in the ligature of the femoral veins or the inferior cava, which is the palliative procedure. Its main differences are the possibility of evolving severe cardiovascular failure during operation, thrombosis of the inferior cava and chronic venous insufficiency of inferior members (MSIS) in the postoperative period. Besides, ligature of the inferior cava is not at all a guarantee against reiterative thromboembolisms.

Another characteristic of the direct procedure in the femoral and iliac veins and inferior cava thromboectomy, i.e., the best procedure having a high eliminating and preventive capacity, is that, it is a radical procedure. Thromboectomy not only permits excision of the floating thrombi, but also reconstruction of the blood flow in the vein affected by severe occclusive thrombosis.

Immediately after thromboectomy, different procedures are applied for the partial occlusion of the inferior cava, which can also be used as unique procedures to prevent thromboembolism.

There is also a procedure for implanting a Mobin-Uddir cava-filter or parasol-filter through the inner jugular vein. This procedure is highly advantageous over all the others and is being widely used clinically, since hardly no trauma is caused with simple prophylatic procedures.

Another procedure, having the same principle as the former, consists in installing a Pate spring, inserting it through the femoral vein, although it has not been so widely used.

Indirect procedures to prevent thromboembolism are preferred, due to the simplicity thereof, but the ulterior results can be identical to those of ligature, that is, the occlusion of the inferior cava due to the obstruction of the cava-filter, which furthermore impedes recanalization of the cavity of the thrombotized vein.

In short, it is necessary to point out that a new procedure of excising floating thrombi from the femoral and iliac vein and the inferior cava, without practising laparotomy, could solve a part of the problem of the prophylaxis of massive pulmonary thromboembolism, which problem is solved with the surgical instrument of the present invention.

The mentioned instrument comprises two tubes arranged in a parallel, back-to-back relationship, one of which is straight and longer than the other which has an oblique bending located close to one of the ends of the longer tube. Inside the longer tube there is a sliding rod which extends along the entire length thereof and which has, at its end protruding from the tube, an operating loop.

At the end of the longer tube, close to the protruding end of the rod, there are placed two additional rings secured at a diametrically opposed position to a widening of the tube itself.

The inner end of the mentioned rod is provided with a clamp which presses the ends of an outwardly protruding steel cable, once it has passed through two axial holes of a stopper fixed to the opening of this tube.

The rod is guided without rotation along grooves in the widening of the tube so that, when displaced in an axial direction with respect to the tube, the loop determined by the steel cable is increased or reduced until it is closed.

At the straight end of the shorter tube, arranged in a parallel back-to-back relationship with the former, there is fixed a wire whose free end is rotatingly secured to the mid central point of the loop. Between the opening of the straight section of the shorter tube and the ring determined by the wire forming the loop, there is a tubular network whose generatrix, in contact with the longer tube, is joined thereto in suhc a way that the wire is placed tangentially inwards of the tubular network.

The widening of the longer tube has a screw by means of which the moving position of the rod is fixed.

For a better understanding of the characteristics of the invention, a set of drawings is accompanied to this specification, wherein illustratively and not limiting, the following is represented:

Figure 1:
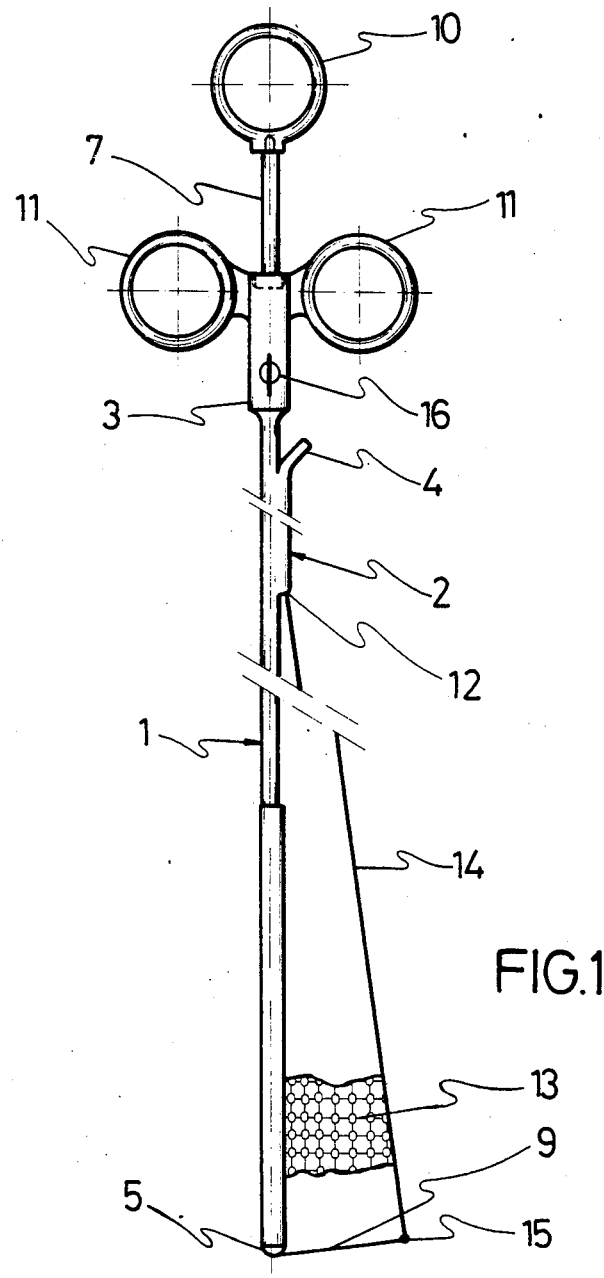
FIG. 1 represents a plan view of the surgical instrument of the present invention.
Figure 2:
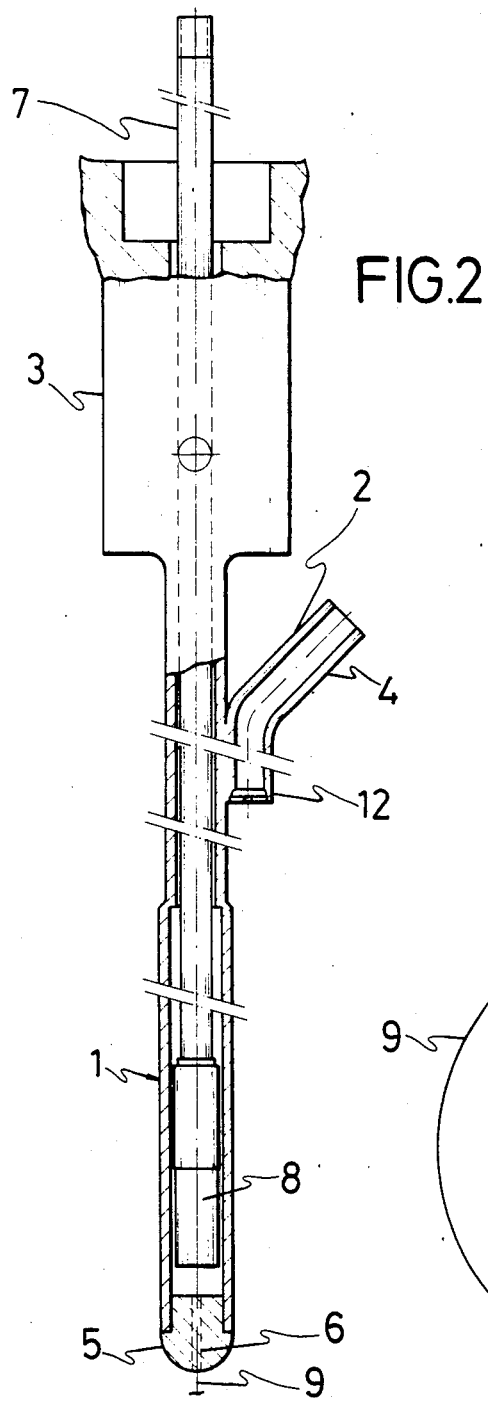
FIG. 2 is an enlarged partial section of FIG. 1.
Figure 3:
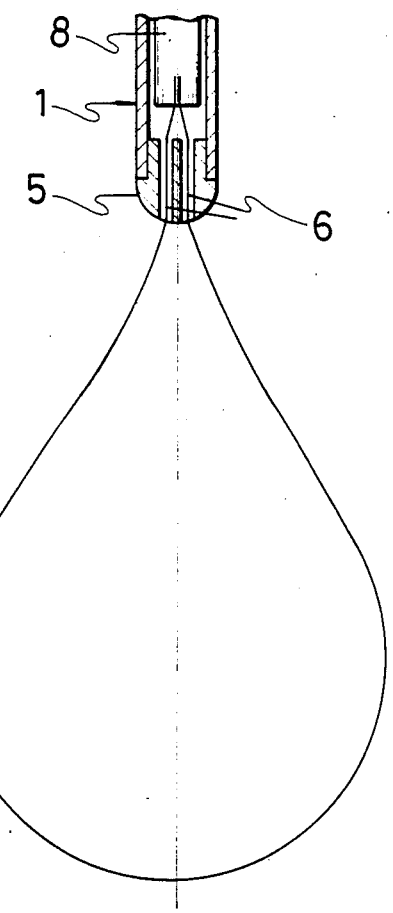
FIG. 3 is a partial section of the end of the longer tube with the steel cable determining the loop in its full protruding position.

Referring to the drawings, there can be seen the surgical instrument for transjugular venous thromboectomy comprising tubes 1 and 2. Tube 1 is longer than tube 2 which is placed close to a widening 3 at the end of the tube 1. Tube 2 is provided with an oblique bending 4 to facilitate access to the interior of the instrument and injection of opacifying substances required for the operation.

At one end of the longer tube 1 there is a stopper 5 provided with two axial holes 6. Through the opposite end corresponding to the widening 3 of tube 1, is inserted a rod 7, the end of which, inserted in tube 1, is provided with a clamp 8 which presses the ends of a steel cable 9 passing through the axial holes 6 of the stopper 5.

The free end of the rod 7, protruding from the widening 3, terminates in a ring 10 for operation thereof, as well as another two rings 11 arranged in diametrically opposed positions and secured to the widening 3 of tube 1.

The opening 12 of the shorter tube 2 presents elements for the engagement of a tubular network 13 and the end of a wire 14 which extends tangentially along the interior of said network 13 and whose free end 15 is rotatingly secured to the mid point of the steel cable 9 forming the loop. The free opening of the tubular network 13 is joined to the steel cable 9 and its generatrix, in contact with tube 1, is secured to this latter.

To fix the position of the rod 7 with respect to the tube 1, there is provided a screw 16 which passes through the wall of the widening 3 of tube 1, pressing and blocking it. The rod 7, in turn, is guided in the widening 3 without rotation along the correspondng grooves.

Upon pushing rod 7 in an axial direction to the tube 1, the steel loop 9, due to its elasticity, opens the oval entrance of the network which is constituted like a bag, the opening of which is enlarged whilst the wall of the inferior vena cava, wherein the instrument has previously been placed, is widened. Upon pulling the rod 7, the entrance to the network 13 is closed, thereby facilitating excision of the floating and/or occlusive thrombi from the vein.

The surgical instrument comprised of a balloon-catether within the bag formed by the tubular network 13 is inserted through the outer hole of the shorter tube 2, so that the lower end of the balloon-catether coincides with the end of the longer tube 1.

When rod 7 is with drawn, pulling ring 10, the end of the balloon-catether makes a slight appearance at the opening of the bag.

Once the phlebotomy of the inner jugular has been practised, the guide has been placed in the inferior cava and the instrument has been positioned at the selected site, the ring 10 is pushed, wherefore the loop 9 opens and, therefore, the venous stream passes through the tubular network 13. The balloon-catether is placed beneath the floating thrombi and penetrates into the soft thrombic masses, beyond the distal limit of the thrombosis.

Once the opacifying substance has been injected through the balloon-catether introduced through the shorter tube 2, the balloon is inflated, wherefore upon pulling, the thrombus breaks away from its base, being hauled and introduced inside the bag.

Thus, once the balloon has been deflated, the instrument can be withdrawn together with the bag filled with thrombi.

The wall of the bag can even be impermeable, the blood flow passing about the instrument and the thrombi can be destroyed by trituration at the place of origin, since the suitable instruments reach the interior of the bag.

The instrument of the present invention facilitates thromboectomy of the inferior vena cava and iliac and femoral veins through the peripheral access, which is advantageous since current laparotomy procedures, causing a high percentage of postoperative morality, are substituted, and it also enlarges the group of patients to be operated.

In cases of floating thrombi at the previously mentioned sites, this instrument also prevents the procedures of partial occlusion of the inferior vena cava with the subsequent risks involved therein.

I claim:

1. A surgical instrument for use in transjugular venous thromboectomy, comprising a shorter tube and a longer tube in a parallel, back-to-back relationship, each of said tubes having two ends, a first end of said longer tube having a widening provided with a first handle means, a second end of the longer tube terminating in a stopper provided with two axial holes, a first end of the shorter tube having an oblique bending close to a point at which the longer tube widens, a second end of said shorter tube terminating at a distance before the second end of the longer tube; a rod within the longer tube, a first end of which, protruding from the widening, terminates in a second handle means, and a second end of which is connected to a clamp means which presses two ends of a steel cable passing through the axial holes of the stopper, thereby forming a loop whose eye may be increased or reduced until it is closed, axial displacement of the rod being guided, without rotation, by grooves in the widening of said longer tube; a wire fixed at a first end thereof to the second end of the shorter tube, a second end of said wire being rotatingly secured to a midpoint of the loop; a tubular network, one side of which is attached to the longer tube, one end of a second side of which is fixed to the second end of the shorter tube and a second end of said second side of which is fixed to the steel cable forming the loop, the wire being placed inside the network; and a screw means for fixing position of the rod after movement thereof relative to said first tube.

2. A surgical instrument according to claim 1 wherein said first handle means comprises two side rings in diametrical opposition.

3. A surgical instrument according to claim 1 wherein said second handle means comprises a ring.

* * * * *

UNITED STATES PATENT AND TRADEMARK OFFICE
CERTIFICATE OF CORRECTION

PATENT NO. : 4,669,464

DATED : June 2, 1987

INVENTOR(S) : Eugenio Ponomar Sulepov

It is certified that error appears in the above-identified patent and that said Letters Patent is hereby corrected as shown below:

Title page

Inventor, Item [76]

delete "P" and replace therefor:

--Ponomar --

Signed and Sealed this

Third Day of May, 1988

Attest:

DONALD J. QUIGG

Attesting Officer

Commissioner of Patents and Trademarks